(12) United States Patent
Steuer et al.

(10) Patent No.: US 6,582,656 B1
(45) Date of Patent: *Jun. 24, 2003

(54) SYSTEM AND METHOD FOR NONINVASIVE HEMODYNAMIC MEASUREMENTS IN HEMODIALYSIS SHUNTS

(75) Inventors: Robert R. Steuer, Pleasant View, UT (US); David R. Miller, Morgan, UT (US)

(73) Assignee: In-Line Diagnostics Corporation, Riverdale, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/536,475

(22) Filed: Mar. 28, 2000

Related U.S. Application Data

(63) Continuation of application No. 08/984,095, filed on Dec. 3, 1997, now Pat. No. 6,117,099, which is a continuation-in-part of application No. 08/955,606, filed on Oct. 22, 1997, now abandoned.
(60) Provisional application No. 60/029,587, filed on Oct. 23, 1996.

(51) Int. Cl.⁷ .......................... A61M 1/14; A61M 37/00; C02F 1/44
(52) U.S. Cl. ...................... 422/44; 604/4.01; 604/5.01; 210/646
(58) Field of Search ............................... 604/4.01, 5.01, 604/6.01, 6.16, 65, 6.11, 8, 19, 28; 422/44, 82.09; 600/366, 368–70, 454, 504; 128/898; 210/646–47, 745, 94, 96.1, 96.2, 321.71, 805, 739, 138–39, 321.6; 436/56, 68; 73/861.07–861.08, 861.11, 861.16, 53.01, 54.15, 54.17, 61.64, 863

(56) References Cited

U.S. PATENT DOCUMENTS

| 3,638,640 | A | 2/1972 | Shaw |
| 4,014,321 | A | 3/1977 | March |
| 4,081,372 | A | 3/1978 | Atkin et al. |

(List continued on next page.)

FOREIGN PATENT DOCUMENTS

| EP | 0 104 772 | 4/1984 |
| EP | 0 160 768 | 11/1985 |
| EP | 0 416 808 A | 3/1991 |
| EP | 0 532 432 A | 3/1993 |
| EP | 0 693 297 A | 1/1996 |
| WO | WO 86/06946 | 12/1986 |
| WO | WO 89/10758 | 3/1989 |

OTHER PUBLICATIONS

T.A. Depner et al., "Hemodialysis Access Recirculation Measured by Ultrasound Dilution," *ASAIO Journal*, vol. 41, No. 3, pp. 749–753 (Jul. 1995).

(List continued on next page.)

*Primary Examiner*—Angela D. Sykes
*Assistant Examiner*—Patricia Bianco
(74) *Attorney, Agent, or Firm*—Jacobson Holman PLLC

(57) ABSTRACT

Access recirculation in a shunt is determined quantitatively by a method in which a standard solution, such as a saline, is injected into a patient's bloodstream upstream of the shunt. At a point in the access line, a photometric measurement is conducted of the change in hematocrit ($\Delta H$) with respect to time. Electronic circuitry receives signals from the detector and compares the integrated area of $\Delta H$ with respect to time of the standard solution initially flowing through the access and of the recirculated solution and provides display of access recirculation. In another aspect, access recirculation and access blood flow are quantitatively determined without injecting a solution into the bloodstream. In this aspect the extent of access recirculation and/or access blood flow is determined quantitatively by a method in which the dialyzer blood flow rate or the ultrafiltration rate (UFR) is changed and the corresponding change in concentration of a blood constituent is measured. In this technique, the concentration of a blood constituent is measured as a function of dialyzer blood flow rate or UFR and electronic circuitry converts these measurements into quantitative determinations of access recirculation and/or access blood flow that can be displayed.

5 Claims, 5 Drawing Sheets

U.S. PATENT DOCUMENTS

| | | |
|---|---|---|
| 4,086,915 A | 5/1978 | Kofsky et al. |
| 4,181,610 A | 1/1980 | Shintani et al. |
| 4,223,680 A | 9/1980 | Jöbsis |
| 4,266,554 A | 5/1981 | Hamaguri |
| 4,295,470 A | 10/1981 | Shaw et al. |
| 4,416,285 A | 11/1983 | Shaw et al. |
| 4,446,871 A | 5/1984 | Imura |
| 4,653,498 A | 3/1987 | New et al. |
| 4,685,464 A | 8/1987 | Goldberger et al. |
| 4,714,080 A | 12/1987 | Edgar, Jr. et al. |
| 4,770,179 A | 9/1988 | New et al. |
| 4,805,623 A | 2/1989 | Jöbsis |
| 4,824,242 A | 4/1989 | Frick et al. |
| 4,825,872 A | 5/1989 | Tan et al. |
| 4,825,879 A | 5/1989 | Tan et al. |
| 4,832,484 A | 5/1989 | Aoyagi et al. |
| 4,867,557 A | 9/1989 | Takatani et al. |
| 4,925,299 A | 5/1990 | Meisberger et al. |
| 5,028,787 A | 7/1991 | Rosenthal et al. |
| 5,054,487 A | 10/1991 | Clarke |
| 5,057,695 A | 10/1991 | Hirao et al. |
| 5,066,859 A | 11/1991 | Karkar et al. |
| 5,092,836 A | 3/1992 | Polaschegg |
| 5,101,825 A | 4/1992 | Gravenstein et al. |
| 5,111,817 A | 5/1992 | Clark et al. |
| 5,312,550 A | 5/1994 | Hester |
| 5,331,958 A | 7/1994 | Oppenheimer |
| 5,351,686 A | 10/1994 | Steuer et al. |
| 5,372,136 A | 12/1994 | Steuer et al. |
| 5,442,969 A | 8/1995 | Troutner et al. |
| 5,453,576 A | 9/1995 | Krivitski |
| 5,456,253 A | 10/1995 | Steuer et al. |
| 5,499,627 A | 3/1996 | Steuer et al. |
| 5,507,723 A | 4/1996 | Keshaviah |
| 5,510,717 A | 4/1996 | Buffaloe et al. |
| 5,518,623 A | 5/1996 | Keshaviah et al. |
| 5,662,806 A | 9/1997 | Keshaviah et al. |
| 5,685,989 A | 11/1997 | Krivitski et al. |
| 6,117,099 A * | 9/2000 | Steuer et al. ............ 422/44 |

OTHER PUBLICATIONS

T.A. Depner et al., "Clinical Measurement of Blood Flow in Hemodialysis Access Fistulae and Grafts by Ultrasound Dilution," *ASAIO Journal*, vol. 41, No. 3, pp. 745–749 (Jul. 1995).

R.A. Sherman et al., "Rate–Related Recirculation: The effect of Altering Blood Flow on Dialyzer Recirculation," *American Journal of Kidney Diseases*, vol. 17, No. 2, pp 170–173 (1991).

J.P. Payne and J.W. Severinghaus, Eds., *Pulse Oximetry*, Chapters 1 and 2 (©1986).

John D. Bower and Thomas G. Coleman, "Circulatory Function During Chronic Hemodialysis," vol. XV *Trans. Amer. Soc. Artif. Int. Organs*, 1969, 373–377.

Larry Reynolds, C. Johnson, A. Ishimaru, "Diffuse reflectance from a finite blood medium: applications to the modeling of fiber optic catheters," Sep. 1976, vol. 15, No. 9, *Applied Optics*, pp. 2059–2067.

R.N. Greenwood, C, Aldridge, L. Goldstein, L.R.I. Baker and W.R. Cattell, "Assessment of arteriovenous fistulate from pressure and thermal dilution studies: clinical experience in forearm fistulae," *Clinical Nephrology*, vol. 23, No. 4–1985, pp. 189–197.

R.N. Greenwood, C. Aldridge and W.R. Cattell, "Serial blood water estimations and in–line blood viscometry: the continuous measurement of blood volume during dialysis procedures," *Clinical Science* (1984) vol. 66, pp. 575–583

C. Aldridge, R.N. Greenwood, W.R. Cattell and R.V. Barrett, "The assessment of arteriovenous fistulate created for haemodialysis from pressure and thermal dilution measurements," *Journal of Medical Engineering & Technology*, vol. 8, No. 3, (May/June), pp. 118–124.

L. Goldstein, L. Pavitt, R.N. Greenwood, C. Aldridge, L.R.I. Baker and W.R. Cattell, "The Assessment of Areteriovenous Fistulae From Pressure and Recirculation Studies," *ProcEDTNA–ERCA* (1985) vol. 14., pp. 207–215.

R.N. Greenwood, C. Aldridge, L. Goldstein, L.R.I. Baker and W.R. Cattell, "Assessment of Arteriovenous Fistulas From Pressure and Recirculation Studies: Clinical Experience In 215 Upper Limb Fistulas," ProcEDTA–ERA (1985), vol. 22, pp. 296–302.

Joseph M. Schmitt, James D. Meindl and Frederick G. Mihm, "An Integrated Circuit–Based Optical Sensor for In Vivo Measurement of Blood Oxygenation," *IEEE Transactions On Biomedical Engineering*, vol. BME–33, No. 21, Feb. 1986, pp. 98–107.

Joseph M. Schmitt, Fred G. Mihm and James Meindl, "New Methods for Whole Blood Oximetry", *Annals of Biomedical Engineering*, vol. 14, pp. 35–52, 1986.

Mark R. Arnfield, J. Tulip and Malcolm McPhee, "Optical Propagation in Tissue With Anisotropic Scattering," *IEEE Transactions on Biomedical Engineering*, vol. 35, No. 5, May 1988, pp. 372–381.

A.C. Guyton, *Textbook of Medical Physiology*, Sixth Edition, pp. 287, 1981.

R.L. Hester, *American Journal of Kidney Disease* 20:6, 1992, pp. 598–602.

Germain, "Simplified Accurate Measurement of Access Recirculation with an In–Line Hematocrit," *Journal of the American Society of Nephrology*, vol. 6, No. 3, p. 489 (1995).

Lindsay, "A Device and a Method for Rapid and Accurate Measurement of Access Recirculation," *Kidney International*, vol. 49, No. 4, pp. 1153–1160 (1996).

* cited by examiner

SYSTEM AND METHOD FOR NONINVASIVE HEMODYNAMIC MEASUREMENTS IN HEMODIALYSIS SHUNTS

CROSS-REFERENCE TO RELATED APPLICATION

This is a continuation of Ser. No. 08/984,095, filed Dec. 3, 1997, now U.S. Pat. No. 6,117,099, which is a continuation-in-part application of U.S. application Ser. No. 08/955,606, filed Oct. 22, 1997, abandoned, which in turn claims priority to U.S. Provisional Application No. 60/029,587, filed Oct. 23, 1996.

FIELD OF THE INVENTION

This invention relates to systems and methods for noninvasively measuring hemodynamic access, access recirculation and blood flow measurements during hemodialysis. More particularly, the present invention relates to noninvasive spectrophotometric systems and methods for quantitatively measuring the shunt (access) recirculation, the access blood flow rate, the dialysis machine blood flow rate and the volumes of priming fluids required by the hemodialysis tubing lines.

INTRODUCTION

Modern medical practice utilizes a number of procedures and indicators to assess a patient's condition especially in the dialysis setting. Hemodialysis is a process wherein an artificial kidney is required to function in the place of the patient's normal kidney in order to remove certain biologic waste products. When the human kidney no longer functions correctly removing waste products such as urea, potassium, and even excess water, blood must be removed from the patient via blood tubing lines and filtered through an artificial kidney or dialyzer. In this process blood is passed through the dialyzer, cleansed, then returned to the normal circulatory system of the patient. Access to the patient's circulatory system is achieved through the use of a surgically implanted shunt or fistula. This "access site" is typically located in the arm, leg, or neck of the patient. Typically needles are placed into this "access" in such a way as to facilitate the easy removal of blood on the "arterial" or upstream side of the dialyzer and typically return the purified blood downstream of the first needle placement on the "venous" side. Unfortunately, in many cases the fistula, or shunt, will clot or "stenos" over time. This results in decreased blood flow through the access which ultimately necessitates either angioplasty or a surgical replacement of the shunt. As the shunt ceases or "clots off" part of the purified dialyzed blood is forced to flow back into the arterial withdrawal site and, hence, recirculates only to be dialyzed again; this is termed "access recirculation". As this recirculation of purified blood continues, the rest of the patient's circulating blood is not adequately cleansed and, hence, an inadequate delivery of the dialysis dosage is provided to the patient.

Therefore, because of the possibility of inadequate dialysis dosage due to this direct recirculation of purified blood back to the withdrawal site, various techniques and methods have been designed to determine:

1) The degree or percentage of access recirculation;
2) The actual blood flow rate in the shunt per se; and
3) The dialyzer blood flow rate itself.

Medical professionals desire to know these three parameters not merely qualitatively, but quantitatively in order to determine the presence and degree of clotting or stenosis. These parameters are desired to predict when the access is beginning to fail and to determine the need for access revision by surgery. Blood flow, Q, measured by the so-called Ficke dilutional techniques, has been described by A. C. Guyton, Textbook of Medical Physiology, Sixth Edition, pg. 287, 1981, wherein Q equals the volume of the injected diluent divided by the mean concentration of the diluent times the duration of the passage of the diluent through the vessel. A dilution curve is obtained by continuously monitoring changes in a given physical parameter of the blood over the time period of the injection. The change in the concentration of either the diluent (or the media) is measured over time.

Hester, R. L. et al., American Journal of Kidney Disease 20:6, 1992, pp. 598–602, have shown that when the dialyzer blood lines are reversed, enhanced blood recirculation occurs. Krivitski, in European patent application number WO9608305A1, indicates that blood line reversal (causing forced recirculation) allows for the determination of the actual blood flow in the shunt.

One method of measuring access blood flow utilizes color coded duplex sonography. However, this technique is expensive. It involves highly trained professionals and the measurements suffer from operator error. The limitations due to variations in the blood vessel diameter and even the Doppler flow angle complicate this measurement.

Another method involves injection of a saline solution intravenously and recording optical detecting the change in the intensity of light passed through a conduit at a point upstream from the injection point (U.S. Pat. No. 5,312,550).

Another technique involves injecting saline boluses into the arterial and venous dialyzer tubing lines and measuring the change of ultrasound velocity (U.S. Pat. No. 5,453,576). This technique is sensitive to changes in temperature, plasma protein levels, and other intrinsic factors that change the density of the blood. Of more significance, however, is that the measurements of the absolute ultrasound velocity changes are influenced not only by the intrinsic blood factors, but also by the unknown mechanical properties of the tubing line per se. In order to compensate for those intrinsic and extrinsic physical problems an additional calibration injection of saline is generally required in the opposite tubing line, whether arterial or venous, thereby producing relative changes in the degree of dilution that occurs due to the saline bolus. Hence, the unknown ultrasound characteristics of the tubing line and other physical, dimensional characteristics can be minimized.

The present standard measurement for access recirculation requires three blood urea nitrogen samples from the patient while on dialysis. However, in addition to the blood samples required from the patient, nursing time, laboratory costs, and appropriate blood flow rates must be maintained during the actual sampling procedure to assure correct urea nitrogen measurements.

Thus, there remains a need for systems and methods for noninvasively and quantitatively determining a patient's hemodynamic access blood flow and blood recirculation parameters.

OBJECTS OF THE INVENTION

Thus, it is an object of the present invention to provide a system and method for noninvasive access hemodynamic monitoring that requires minimal nursing time and no discreet blood sampling.

It is another object of the present invention to provide a system and method for the display of both immediate and continuous visual information regarding the saline dilutional hemodynamic access data.

It is yet another object of the present invention to provide repeatable and reliable systems and methods for the noninvasive determination of the hemodynamic access flow properties under varying conditions including: different ultrafiltration rates, patient postures, tubing types and dimensions, and even different dialyzer membranes and dialysis delivery systems.

Another object of the present invention is to provide a means and method of quantitatively determining the volumetric blood flow rate actually passing through the dialyzer, $Q_i$.

Another object of the present invention is to present the dilutional concentration-time curves to the operator by visual, real-time display means.

Still another object of the present invention is to provide a system and method which can provide immediate and quantitative determination of the actual volume of fluid necessary to prime the dialyzer circuit.

It is likewise another object of the present invention to provide a system and method for determining the access blood flow and access recirculation that does not require the injection of saline. For example, by changing the ultrafiltration rate (UFR) or dialyzer blood flow rate. It is another object of the present invention to provide a system and method for measuring dialyzer blood flow parameters.

These and other objects and advantages of the invention will become more fully apparent from the description in the claims which follow or may be learned by the practice of the invention.

SUMMARY OF THE INVENTION

In one aspect of the present invention, access recirculation in a shunt is determined quantitatively by a method in which a standard solution, such as a saline solution, is injected into the patient's bloodstream at a point upstream of the shunt. At a point in the access line, a photometric measurement is conducted of the change in hematocrit ($\Delta H$) with respect to time. Electronic circuitry receives signals from the detector and compares the integrated area of $\Delta H$ with respect to time of the standard solution initially flowing through the access and of the recirculated solution and provides a nearly instantaneous display of the amount of access recirculation.

In another aspect of the present invention, the access recirculation and/or access blood flow are quantitatively determined without injecting a solution into the bloodstream. In this aspect the extent of access recirculation and/or access blood flow is determined quantitatively by a method in which the dialyzer blood flow rate or the ultrafiltration rate (UFR) is changed and the corresponding change in concentration of a blood constituent is measured. In this technique, the concentration of a blood constituent is measured as a function of dialyzer blood flow rate or UFR and electronic circuitry converts these measurements into quantitative determinations of access recirculation and/or access blood flow that can be displayed nearly instantaneously. In a preferred embodiment the measured blood constituent is red blood cells.

DETAILED DESCRIPTION OF THE INVENTION

In a preferred embodiment, measurements are conducted using the apparatus described in U.S. Pat. Nos. 5,456,253 and 5,372,136, which are incorporated herein as if reproduced in full below. Both of these patents form part of the present disclosure.

Thus, in a preferred embodiment, hematocrit is measured through blood in a flow through cuvette located in the access line. In a preferred embodiment, the apparatus and signal manipulations described in U.S. Pat. No. 5,372,136 are used to measure hematocrit. The numbered components are the same as FIG. 1 in U.S. Pat. No. 5,456,253.

Figure 1:
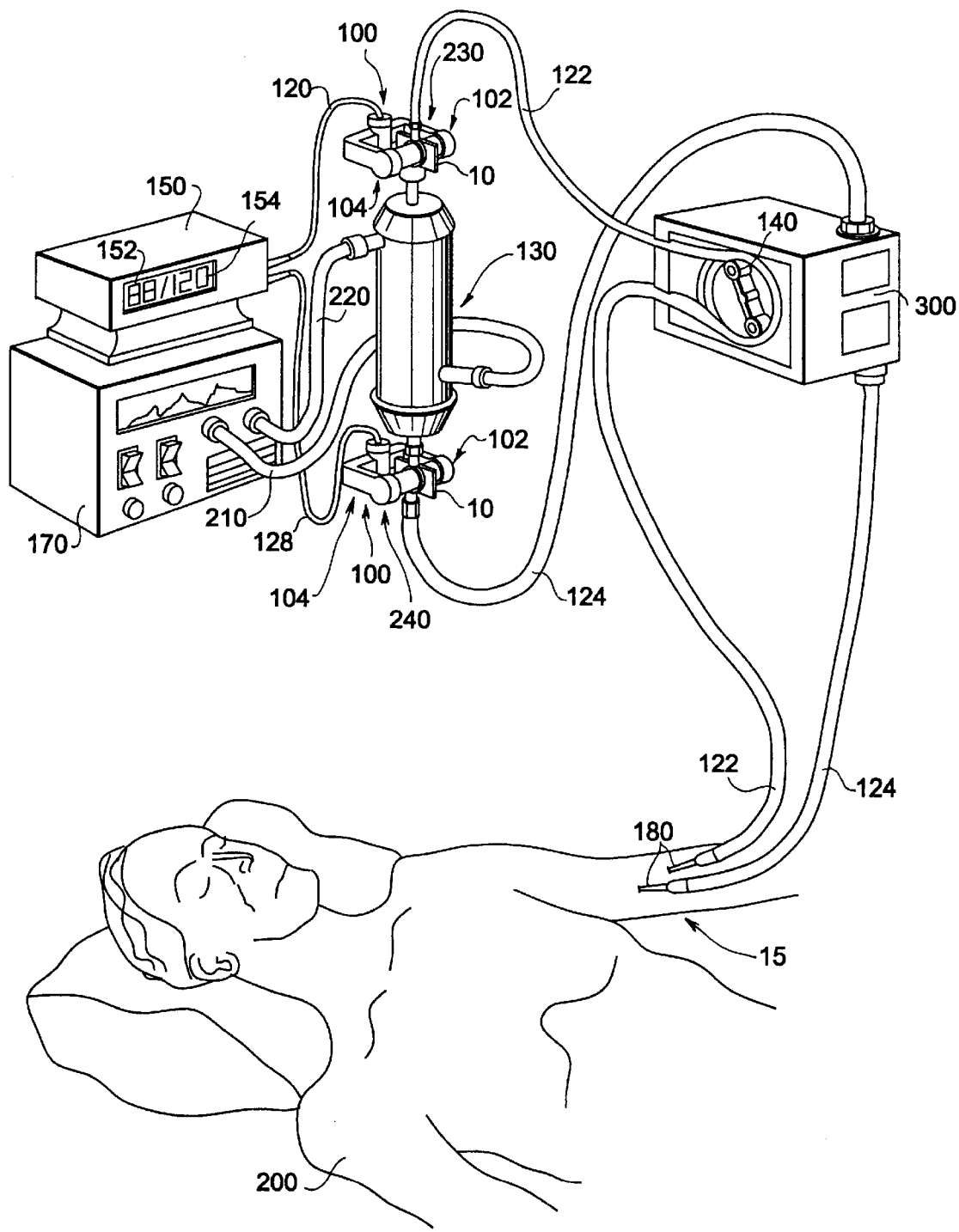
FIG. 1 shows a typical dialysis tubing connection circuit.

In hemodialysis, blood is taken out of a patient 200 by an intake catheter means, one example of which is shown in FIG. 1 as an input catheter 122. Input catheter 122 is intravenously inserted into patient 200 at a site 180 and is used for defining a blood passageway upstream of a blood filter used to filter the impurities out of the blood. The blood filter is also called a dialyzer 130. The unclean blood flows from an artery in patient 200 to a pump means, an example of which is pump 140. From pump 140, the blood flows to dialyzer 130. Dialyzer 130 has an input port 230 and an output port 240. The pump 140 performs the function of moving the unclean blood from patient 200 into input port 230, through dialyzer 130, and out of dialyzer 130 at output port 240.

Specifically, unclean blood in input catheter 122 is transported to input port 230 of dialyzer 130. After passing through and being cleansed by dialyzer 130, the blood may receive further processing, such as heparin drip, in hemodialysis related component 300. The now clean blood is returned to patient 200 after the dialyzing process by means of an output catheter means, an example of which is output catheter 124. Output catheter 124, which is also intravenously inserted into patient 200 at site 180, defines a blood passageway which is downstream from dialyzer 130, taking the blood output by dialyzer 130 back to patient 200.

As mentioned, the hemodialysis process uses a blood filter or dialyzer 130 to clean the blood of patient 200. As blood passes through dialyzer 130, it travels in straw-like tubes (not shown) within dialyzer 130 which serve as membrane passageways for the unclean blood. The straw-like tubes remove poisons and excess fluids through a process of diffusion. An example of excess fluid in unclean blood is water and an example of poisons in unclean blood are blood urea nitrogen (BUN) and potassium.

The excess fluids and poisons through an ultrafiltration process are removed by a clean dialysate liquid fluid, which is a solution of chemicals and water. Clean dialysate enters dialyzer 130 at an input tube 210 from a combined controller and tank 170. The dialysate surrounds the straw-like tubes in dialyzer 130 as the dialysate flows down through dialyzer 130. The clean dialysate picks up the excess fluids and poisons passing through the straw-like tubes, by diffusion, and then returns the excess fluids and poisons with the dialysate out of dialyzer 130 via an output tube 220, thus cleansing the blood. Dialysate exiting at output tube 220 after cleansing the blood may be discarded.

In some, unclean blood flows from an artery in patient 200 to pump 140 and then to dialyzer 130. Unclean blood flows into dialyzer 130 from input catheter 122 and clean blood flows out of dialyzer 130 via output catheter 124 back to patient 200.

Installed at either end of dialyzer 130 is a spectrophotometry means for defining a blood flow path, for emitting radiation into the blood in the flow path, and for detecting radiation passing through both the blood and the flow path. The spectrophotometry means includes a cuvette means for defining the blood flow path, and an emitter/detector means for emitting and detecting radiation. Within the emitter/detector means is both an emission means for directing radiation and a detector means for detecting radiation.

In a prior art embodiment as shown in FIG. 1, an example of the emitter/detector means is depicted by the emitter/detector apparatus 100. An example of the emission means is indicated by a photoemitter 102. Emitter/detector apparatus 100 also has a detection means, an example of which is depicted as a photodetector 104. An example of the cuvette means is shown in FIG. 1 as cuvette 10.

Emitter/detector apparatus 100 enables the detection by photodetector 104 of the portion of radiation which is directed by photoemitter 102 to cuvette 10 and passes through both the blood therein and cuvette 10.

As shown in FIG. 1, a cuvette 10 is installed at either end of dialyzer 130. Each cuvette 10 has a photoemitter 102 and a photodetector 104 thereon. In the preferred embodiment of the system, photoemitter 102 and photodetector 104 are shown as being held together by a spring loaded C-Clamp type in emitter/detector photo apparatus 100.

The emitter/detector means is electrically connected to a calculation means. In a preferred embodiment of the system, an example of the calculator means is depicted in FIG. 1 as computer 150 which is electrically connected to photoemitter 102 and photodetector 104 on emitter/detector apparatus 100 by means of cable 120 or 128.

Intake catheter 122 takes blood to cuvette 10 situated before input port 230 of dialyzer 130. Emitter/detector apparatus 100 at input port 230 of dialyzer 130 subjects the blood therein to radiation wavelengths of electromagnetic radiation for the purposes of analysis, via spectrophotometry, so that the concentration of a desired biological constituent can be derived. Each photodetector 104, at both input port 230 and output port 240 of the dialyzer 130. communicates the detected radiation via cable 120 or 128 to computer 150.

Computer 150 calculates both before dialysis (via cable 120) and after dialysis (via cable 128) concentrations of the sought-after or desired biologic constituent. Computer 150 then displays, respectively, at a first display 152 and a second display 154, the derived concentration of the biological constituent in either analogue or digital representations. The calculation means, shown here by example as computer 150, preferably has the multiple capability of simultaneous real-time computation and display of several blood parameters of interest.

1. Single Injection Dilutional Technique

Figure 2:
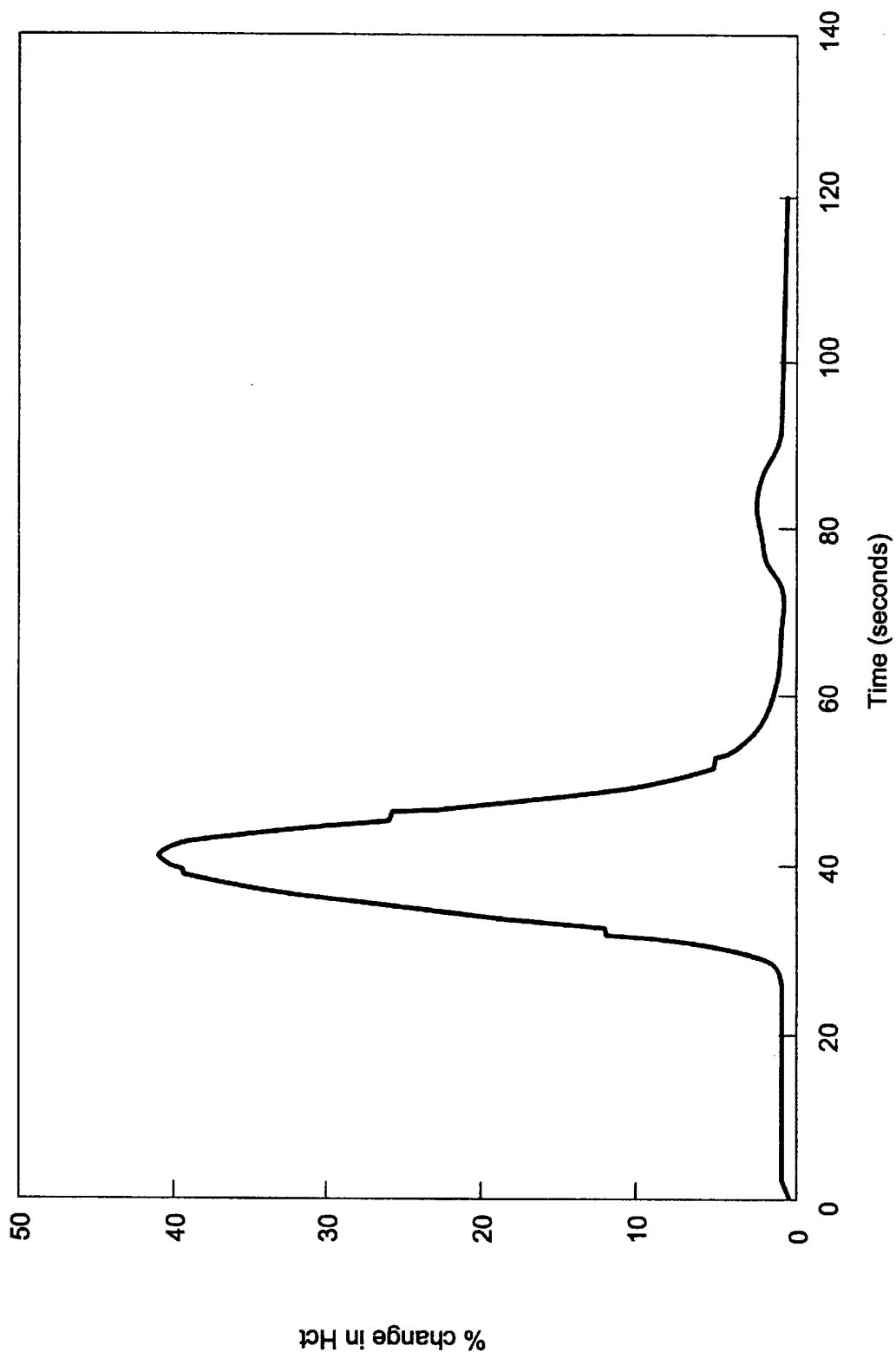
FIG. 2 illustrates a plot of %Δ Hematocrit (or %Δ blood volume (BV)) versus Time following an injection of 10 ml saline into the bloodstream at a location upstream of the shunt.

In the first aspect, approximately 10 mls of saline is injected over five seconds into the arterial line. The measuring disposable blood chamber 10 is immediately downstream (in the arterial line) from the injection point 15, see FIG. 1. A change in hematocrit (ΔH) instantly occurs due to the dilution of the whole blood by the saline. Then, by appropriately measuring and computing the area under the dilution curve, see FIG. 2, (the Ficke principle), the dialyzer blood flow ($Q_i$), access recirculation (AR), and access blood flow ($Q_a$) are determined in the following manner.

$$Q_i = V/K \int (\% \Delta H) dt \quad (1)$$

where:

$Q_i$=Dialyzer blood flow rate, in ml/min

K=a conversion factor, determined empirically to convert percent change hematocrit units to area and minute units.

Figure 3:
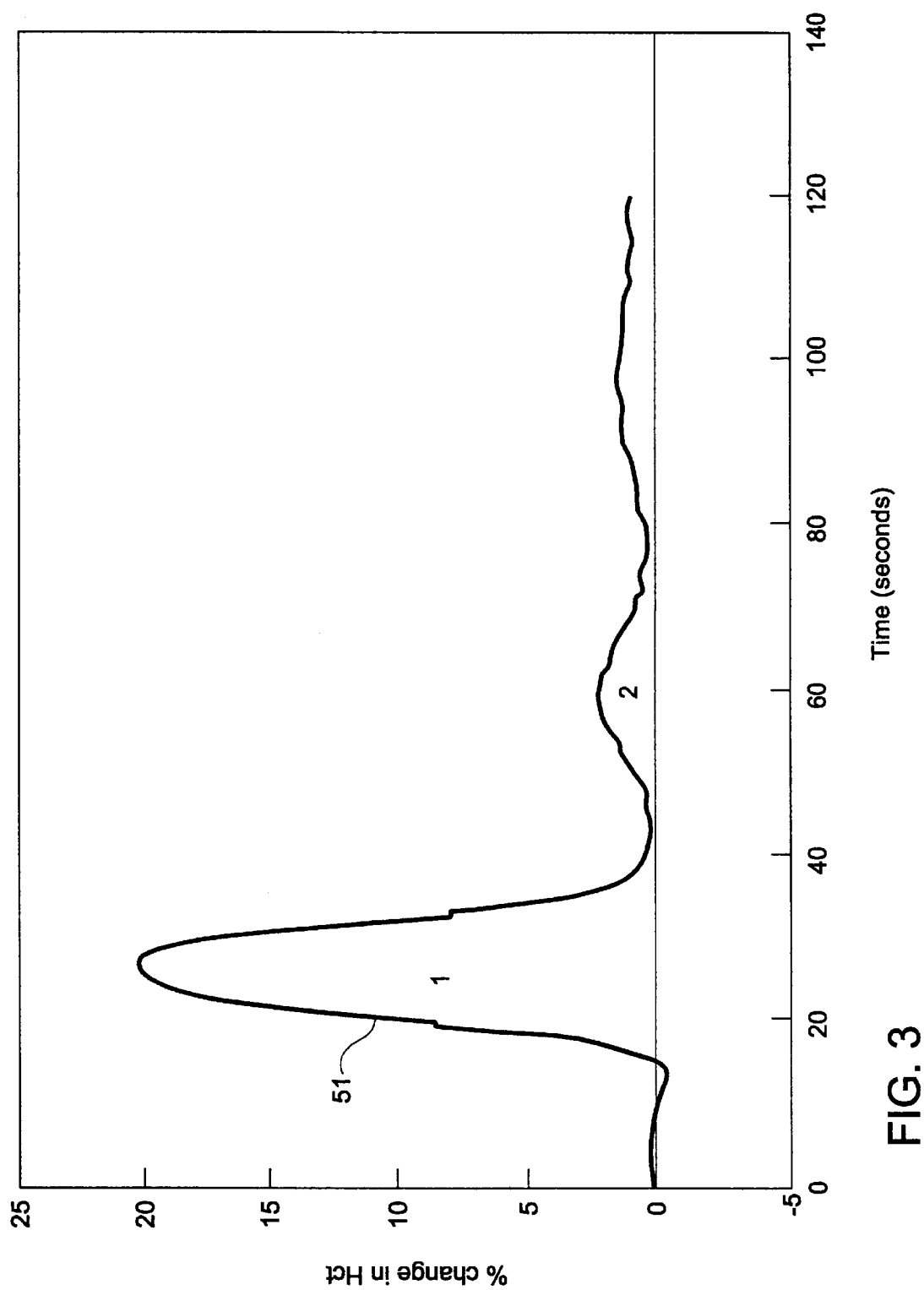
FIG. 3 shows a single injection dilutional curve when access recirculation is present, note the second area (curve 2) following the larger first area (curve 1).

$\int (\% \Delta H) dt$=area under the hematocrit dilution curve (1) in FIG. 3.

V=Volume of saline injected (typically 10 ml)

If access recirculation (AR) is present, FIG. 3 is obtained. In order to determine AR the following equation is used:

$$AR = (\int (\% \Delta H)_2 dt / \int (\% \Delta H)_1 dt) \cdot 100 \quad (2)$$

where:

AR=% Access Recirculation, when ultrafiltration is off $\int (\% \Delta H)_2 dt$=area under curve 2, the "measuring area"

$\int (\% \Delta H)_1 dt$=area under curve 1, the "calibration area"

The area under the dilution curve 1, the "calibration area", represents 100% of the 10 ml saline bolus passing through the chamber and diluting the blood in the path of the optical detector. The area under dilution curve 2, the "measuring area", represents the amount of saline which "recirculated" from the venous line into the shunt (or access) and "back again" to the arterial line and hence, passing the optical detector a second time.

The areas under the dilution curves are measured during specific time intervals in the following way. With reference to FIG. 3, the injection of saline solution takes place at time 0 seconds. The slope of the resulting line 51 remains essentially flat until about 19 seconds, where there is a dramatic increase in the slope of line 51. It is at this point that the system starts to measure the area under curve 1. The system continues to measure the area under curve 1 until the slope of line 51 changes from a negative slope to a zero slope or a positive slope which occurs at about 41 seconds. It is at that point in time that the measurement of curve 1 stops and the measurement of the area of curve 2 begins. The measurement of curve 2 continues until a time is reached where the slope of line 51 changes from a negative to a zero, which in FIG. 3 occurs at about 78 seconds. It is at this point in time that the measurement of the area of curve 2 stops.

Knowing $Q_i$ (in ml/min) and the time interval (T) between dilution curves 1 and 2 of FIG. 3, the priming dialyzer circuit volume (PDCV) can be calculated with the following:

$$PDCV = Q_i T(1/60) \quad (3)$$

Finally, to calculate the access blood flow, the arterial line is reversed with the venous line and placed "downstream" of the venous line in the shunt. A 10 ml saline bolus (given over 5 seconds) is then injected, into the arterial line, as usual, resulting in the dilution curves seen in FIG. 4. As in the determination of access recirculation, the reversed access recirculation (RAR) is computed from the following formula:

$$RAR = \int (\% \Delta H)_2 dt / \int (\% \Delta H)_1 dt \quad (4)$$

and, as in equation 2, ultrafiltration is off.

Once RAR is determined, then the access blood flow, $Q_a$, is calculated from:

$$Q_a = Q_i(RAR^{-1} - 1) \quad (5)$$

Figure 4:
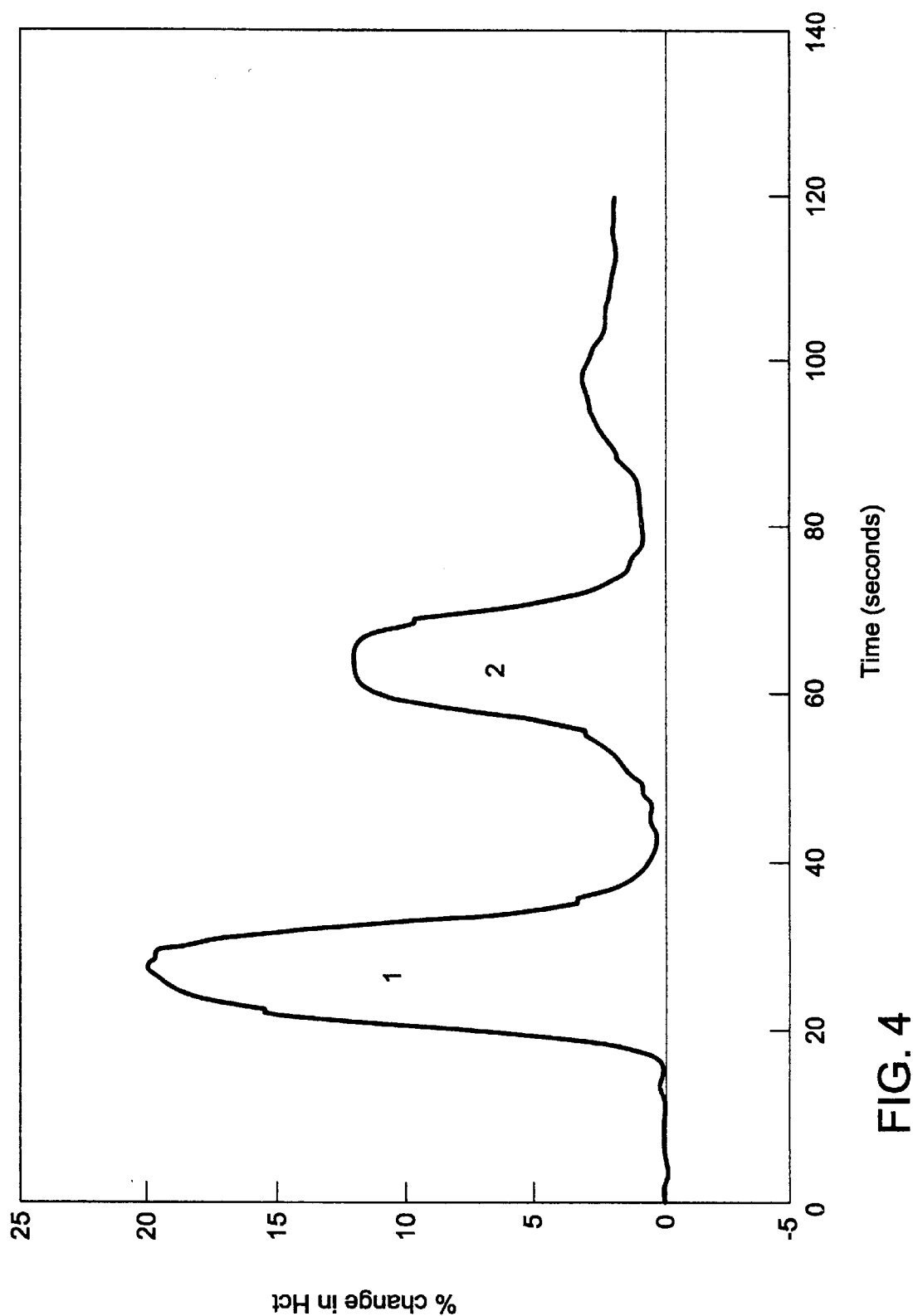
FIG. 4 shows a single injection dilutional curve with the arterial and venous tubing lines reversed causing forced (or reversed) recirculation.

Hence, with a single injection of saline into the arterial line, immediately upstream from the measuring disposable blood chamber, the calibration area (curve 1) and the measuring area (curve 2) are obtained, see FIGS. 3 and 4. A reference, or the calibration area, is already incorporated within the single injected saline bolus, without the need for dual sensors, or a customary second saline injection; where one injection is for reference measurements and the second injection is the measuring injection.

The single saline injection technique utilizing a single detector is a major enhancement and has many advantages. For example, in other methods typically two detectors must be "tuned" exactly the same. In a double injection technique, two separate injections must be the exact same volume each time and given at the same rate of injection, otherwise the calibration areas and the measuring areas will be different, giving erroneous results.

The equation mentioned above requires accurate measurement of the area under the hematocrit dilution curve, $\int(\%\Delta H)dt$. The most common error in that measurement comes from the variations in the rate of injection of the saline bolus (typically 10 ml over 5 seconds). The actual rate of saline injection can be calculated from time base parameters seen in the arterial injection. The resulting variation (or perturbation), $Q_i$, caused by these injection-induced transients is compensated for as seen in equations 5a and 5b (from equation 1):

$$Q_i(\text{corrected}) = V/[K(\text{Area}_m - \text{Area}_p)] \quad (5a)$$

where:
Area$_m$=Area measured under the hematocrit dilution curve
Area$_p$=Area of push rate of the saline injection $$\text{Area}_p = [(-0.018)Q_i(raw) + 1.22]\left[\frac{2013}{span} - Q_i(raw)(0.3661)\right] \quad (5b)$$

where:
$Q_i$(raw)=raw blood flow rate based on area$_m$
span=time interval from the start of the saline injection to the end of the injection, in seconds.

The injection rate-induced transients can thusly be compensated for resulting in more accurate blood flow, access recirculation and access blood flow measurements.

2. The Second Aspect, the Δ Hematocrit Technique

Figure 5:
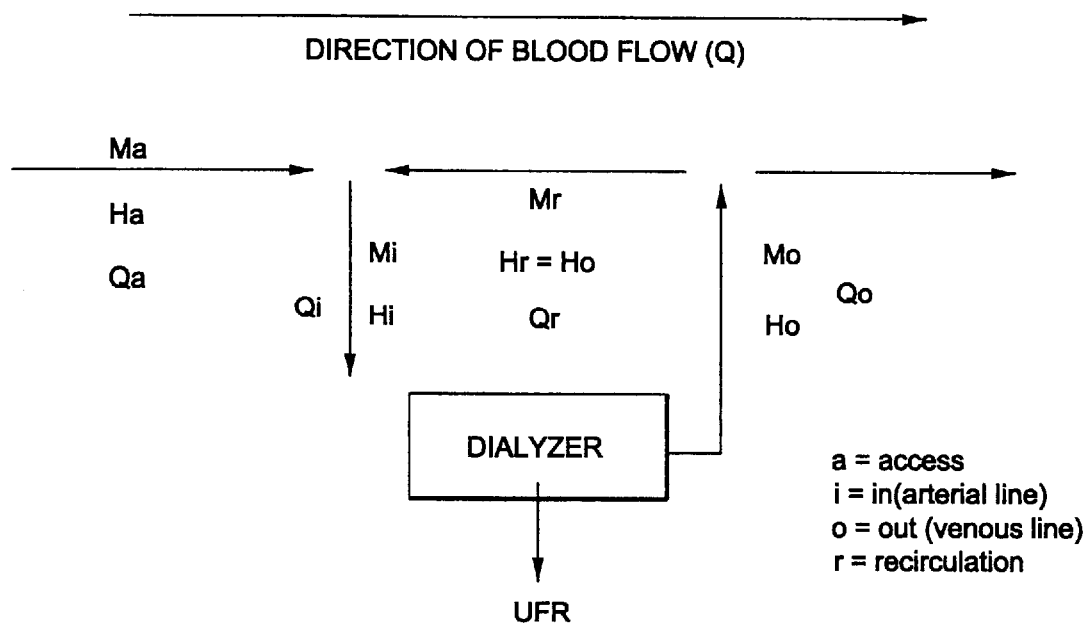
FIG. 5 diagrammatically represents the dialysis circuit in terms of mass flow, in normal arterial, venous line orientation.

Referencing FIG. 5, the following mathematics allows determination of access recirculation via the Δ Hematocrit technique, wherein the following mass (m) and blood flow rate (Q) balance obtains:

$$m_a + m_r = m_i \quad (6)$$

and $$Q_a + Q_r = Q_i \quad (7)$$

so:

$$Q_a H_a + Q_r H_o = Q_i H_i \quad (8)$$

(where $Q_o = Q_i - UFR$) since:

$$Q_i H_i = Q_o H_o = (Q_i - UFR)H_o \quad (9)$$

and $$H_o = (Q_i/(Q_i - UFR))H_i \quad (10)$$

But since: $R = Q_r/Q_i$, dividing equation 8 by $Q_i$ obtaining:

$$H_i/H_a = (1-R)[1 - R(Q_i/(Q_i - UFR))]^{-1} \quad (11)$$

Therefore to determine access recirculation (AR) by the Δ Hematocrit method the following obtains:

$$AR = 100 \cdot (H_i - H_a)[(Q_i/(Q_i - UFR))H_i - H_a]^{-1} \quad (12)$$

From Equation 12 note that by either changing the dialyzer blood flow rate, $Q_i$, or by changing the ultrafiltration rate (UFR) a change in the hematocrit is created; hence, the direct measurement of access recirculation is determined.

Figure 6:
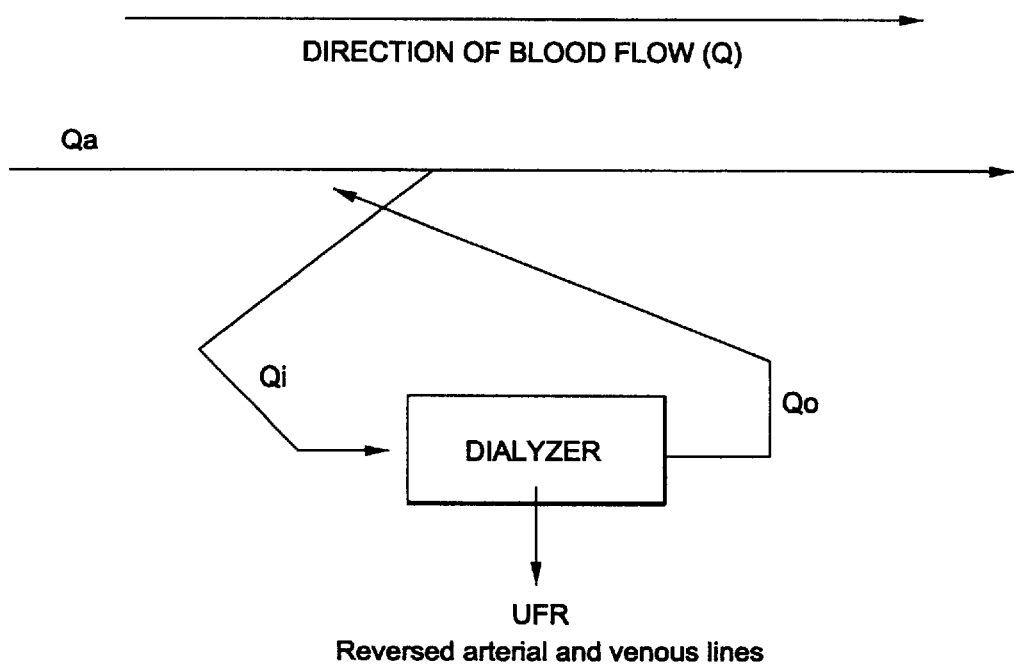
FIG. 6 diagrammatically represents the dialysis circuit in terms of mass flow with arterial and venous lines reversed.

To determine the access blood flow, $Q_a$, by the Δ Hematocrit method refer to FIG. 6, which shows the arterial and venous lines reversed. Since there must be a hematocrit balance around the tubing/dialyzer circuit the following applies:

$$Q_a H_a + Q_o H_o = H_i(Q_a + Q_o) \quad (13)$$

but, $$Q_i H_i = Q_o H_o, \text{ (and } Q_o = Q_i - UFR) \quad (14)$$

so, $$Q_a H_a + Q_i H_i = H_i(Q_a - Q_i - UFR) \quad (15)$$

and $$H_i/H_a = Q_a(Q_a - UFR) \quad (16)$$

Therefore:

$$Q_a = H_i(UFR)/(H_i - H_a) \quad (17)$$

From Equation 17, $Q_a$, by the Δ Hematocrit technique, is independent of the dialyzer blood flow rate, $Q_i$. Therefore, by merely changing the ultrafiltration rate (UFR), access blood flow is directly computed, when the measurement of $H_i$ occurs in the immediately removed portion of the mixed blood (input to the dialyzer).

By way of example, the value of $Q_a$ is determined in the following manner. Assume that UFR=0 milliliters/minute or ml/min. According to equation (17), $Q_a$ would equal 0 m/min. Also with UFR=0 ml/min, the access hematocrit $H_a$ is measured to be 30.0. This becomes the baseline value for $H_a$. When the UFR is increased, as for example, to 30 m/min, the value of the hematocrit in the arterial line, $H_i$, measured after a short period of time, (3 or 4 minutes) is about 31.0. Therefore, according to equation 17, $Q_a = 31(30)/(31-30) = 930$ ml/min.

However, when the measurement of hematocrit occurs in the delivered portion of the mixed blood (output of the dialyzer) the following equations obtain, equation 15 becomes:

$$Q_a H_a + Q_o H_o = H_o \frac{Q_o}{Q_i}(Q_a + Q_o) \quad (18)$$

resulting in:

$$Q_a = \frac{Q_o\left(1 - \frac{Q_o}{Q_i}\right)}{\frac{Q_o}{Q_i} - \frac{H_a}{H_o}} \quad (19)$$

Substituting from (14) yields:

$$Q_a = \frac{(Q_i - UFR)\left(\frac{UFR}{Q_i}\right)}{1 - \frac{UFR}{Q_i} - \frac{H_a}{H_o}} \quad (20)$$

Again when UFR=0 ml/min, hematocrit=$H_a$, and when UFR=30 ml/min, hematocrit=$H_o$. Note also that if the input, $H_i$, and output, $H_o$, are known then:

$$Q_i = \frac{UFR}{1 - \frac{H_i}{H_o}} \quad (21)$$

Without the injection of saline, but by measuring the ΔH on the delivered portion of mixed blood (output of the dialyzer) by merely changing either the UFR or the $Q_i$ to known values, the access blood flow is easily and accurately calculated.

Likewise, if the input (pre dialyzer) and output (post dialyzer) hematocrits are measured then either the $Q_i$ or UFR can be accurately calculated as well.

Utilizing the instantaneous hematocrit monitor, the above Δ Hematocrit method will measure AR and $Q_a$ immediately and directly. Using the Δ Hematocrit method with a blood volume monitor (a relative measure of hematocrit) to measure AR and $Q_a$ will yield immediate and direct results. However, because of the relative measure of hematocrit, the results will not be accurate.

It should be emphasized again that while U.S. Pat. No. 5,372,136 shows the measurement of absolute hematocrit, this technique and method described in the second aspect of the invention is intended to incorporate the relative measure of hematocrit (ΔBV), as well as the usage of single wavelength optical, conductimetric or ultrasonic methods of BV measurements. Therefore, the method of simply changing Qi or UFR in order to measure AR or simply changing UFR to measure the $Q_a$ are important new and unique concepts.

U.S. Pat. No. 5,372,136 clearly defines the operational means whereby the instantaneous and continuous measurement of hematocrit is obtained and used in connection with the disposable blood chamber mentioned above.

Although the foregoing discussion relates to noninvasive analysis of hemodynamic access flow information, it will be appreciated that the above mentioned circuitry and algorithms may be adapted for analysis of other rheologic parameters.

The present invention may be embodied in other specific forms without departing from its intent or essential characteristics. The described embodiments are to be considered in all respects only as illustrative and not restrictive.

What is claimed is:

1. A method for measuring access recirculation in a dialysis system having arterial and venous tubing lines, said method comprising the steps of:

ensuring that the ultrafiltration is off;

changing a blood parameter in the arterial line over a first period of time;

measuring a percentage change in hematocrit over a second period of time;

measuring a percentage change in hematocrit over a third period of time taking place after the second period of time; and comparing the measured change in hematocrit over the third period of time to the measured change in hematocrit over the second period of time to yield a signal that is directly proportional to access recirculation.

2. The method of claim 1 further comprising the steps of:

multiplying the signal by a predetermined factor to yield percentage change in access recirculation.

3. The method of claim 2, wherein said factor is 100.

4. A method for measuring priming dialyzer circuit volume in a dialysis system having arterial and venous tubing lines, said method comprising the steps of:

changing a blood parameter in the arterial line over a first period of time;

measuring a percentage change in hematocrit over a second period of time;

measuring a percentage change in hematocrit over a third period of time;

comparing the changed blood parameter in the aterial line to the product of the measured change in hematocrit over the first period of time and a predetermined conversion factor to yield a signal that is indicative of dialyzer blood flow rate; and multiplying the dialyzer blood flow rate by the sum of the first, second and third periods of time and dividing the result by 60 to yield a signal that is indicative of the priming dialysis circuit volume.

5. A method for measuring access blood flow in a dialysis system having arterial and venous tubing lines, said method comprising the steps of:

changing a blood parameter in the venuous line over a first period of time;

determining dialyzer blood flow rate;

measuring the percentage change in hematocrit over a second period of time;

measuring the percentage change in hematocrit over a third period of time;

comparing the measured change in hematocrit over the third period of time to the measured change in hematocrit over the second period of time to yield a signal that is directly proportional to reversed access recirculation (RAR);

subtracting 1 from the inverse of the RAR and multiplying that result by the dialyzer blood flow rate to yield a signal indicative of access blood flow rate.

* * * * *